(12) United States Patent
Wortzman et al.

(10) Patent No.: US 7,919,483 B2
(45) Date of Patent: *Apr. 5, 2011

(54) METHOD FOR THE TREATMENT OF ACNE

(75) Inventors: Mitchell Wortzman, Scottsdale, AZ (US); R. Todd Plott, Briscoe, TX (US); Kuljit Bhatia, Nesconset, NY (US); Bhiku Patel, Chandler, AZ (US)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 621 days.

This patent is subject to a terminal disclaimer.

(21) Appl. No.: 11/166,817

(22) Filed: Jun. 24, 2005

(65) Prior Publication Data
US 2006/0293290 A1  Dec. 28, 2006
US 2007/0225262 A2  Sep. 27, 2007

(51) Int. Cl.
A61K 9/16 (2006.01)
A61K 9/50 (2006.01)
A61K 9/52 (2006.01)
A61K 9/54 (2006.01)
A61K 31/63 (2006.01)

(52) U.S. Cl. ........ 514/152; 424/482; 424/457; 424/458; 424/455; 424/474; 424/495; 424/497; 424/489; 424/498; 424/490

(58) Field of Classification Search ................. 514/152; 424/482, 457, 458, 455, 474, 490, 495, 497, 424/489, 498
See application file for complete search history.

(56) References Cited

U.S. PATENT DOCUMENTS

| | | |
|---|---|---|
| 3,932,615 A | 1/1976 | Ito et al. |
| 3,957,980 A | 5/1976 | Noseworthy |
| 3,966,922 A | 6/1976 | Okamoto et al. |
| 4,086,332 A | 4/1978 | Armstrong |
| 4,126,680 A | 11/1978 | Armstrong |
| 4,369,172 A | 1/1983 | Schor et al. |
| 4,376,118 A | 3/1983 | Daher et al. |
| 4,443,442 A | 4/1984 | Skillern |
| 4,701,320 A | 10/1987 | Hasegawa et al. |
| 4,764,377 A | 8/1988 | Goodson |
| 4,792,448 A | 12/1988 | Ranade |
| 4,806,529 A | 2/1989 | Levy |
| 4,837,030 A | 6/1989 | Valorose, Jr. et al. |
| 4,925,833 A | 5/1990 | McNamara et al. |
| 4,935,411 A | 6/1990 | McNamara et al. |
| 4,935,412 A | 6/1990 | McNamara et al. |
| 4,960,913 A | 10/1990 | Szalay et al. |
| 5,007,790 A | 4/1991 | Shell |
| 5,122,519 A | 6/1992 | Ritter |
| 5,167,964 A | 12/1992 | Muhammad et al. |
| 5,188,836 A | 2/1993 | Muhammad et al. |
| 5,202,128 A | 4/1993 | Morella et al. |
| 5,209,978 A | 5/1993 | Kosaka et al. |
| 5,211,958 A | 5/1993 | Akkerboom et al. |
| 5,217,493 A | 6/1993 | Raad et al. |
| 5,230,895 A | 7/1993 | Czarnecki et al. |
| 5,262,173 A | 11/1993 | Sheth et al. |
| 5,277,916 A | 1/1994 | Dwyer et al. |
| 5,283,065 A | 2/1994 | Doyon et al. |
| 5,300,304 A | 4/1994 | Sheth et al. |
| 5,324,751 A | 6/1994 | DuRoss |
| 5,348,748 A | 9/1994 | Sheth et al. |
| 5,413,777 A | 5/1995 | Sheth et al. |
| 5,459,135 A | 10/1995 | Golub et al. |
| 5,518,730 A | 5/1996 | Fuisz |
| 5,554,654 A | 9/1996 | Yu et al. |
| 5,582,837 A | 12/1996 | Shell |
| 5,665,776 A | 9/1997 | Yu et al. |
| 5,674,539 A | 10/1997 | Tomas |
| 5,776,489 A | 7/1998 | Preston et al. |
| 5,780,049 A | 7/1998 | Dickner et al. |
| 5,800,836 A | 9/1998 | Morella et al. |
| 5,814,331 A | 9/1998 | Holen |
| 5,834,450 A | 11/1998 | Su |
| 5,855,904 A | 1/1999 | Chung et al. |
| 5,908,838 A | 6/1999 | Gans |
| 5,972,389 A | 10/1999 | Shell et al. |
| 6,087,382 A | 7/2000 | Bonner, Jr. et al. |
| 6,120,803 A | 9/2000 | Wong et al. |
| 6,165,513 A | 12/2000 | Dansereau et al. |
| 6,165,999 A | 12/2000 | Vu |
| 6,194,000 B1 | 2/2001 | Smith et al. |
| 6,340,475 B2 | 1/2002 | Shell et al. |
| 6,340,476 B1 | 1/2002 | Midha et al. |
| 6,429,204 B1 | 8/2002 | Golub et al. |
| 6,455,583 B1 | 9/2002 | Pflugfelder et al. |
| 6,497,902 B1 | 12/2002 | Ma |

(Continued)

FOREIGN PATENT DOCUMENTS

CA 2025703 9/1990

(Continued)

OTHER PUBLICATIONS

American Hospital Formulary SErvice Drug Information 88, 1988, pp. 330-331.*

(Continued)

*Primary Examiner* — Jennifer M Kim

(74) *Attorney, Agent, or Firm* — Ohlandt, Greeley, Ruggiero & Perle, L.L.P.

(57) ABSTRACT

A method for treatment of acne with tetracyclines is provided. A lower sustained dose and no loading dose is employed, with an optional once-a-day dosing regimen.

6 Claims, No Drawings

U.S. PATENT DOCUMENTS

| | | | |
|---|---|---|---|
| 6,638,922 B2 | 10/2003 | Ashley et al. | |
| 6,673,843 B2 | 1/2004 | Arbiser | |
| 6,863,830 B1 | 3/2005 | Purdy et al. | |
| 6,958,161 B2 | 10/2005 | Hayes et al. | |
| 7,008,631 B2 | 3/2006 | Ashley | |
| 7,211,267 B2 | 5/2007 | Ashley | |
| 2002/0015731 A1 | 2/2002 | Appel et al. | |
| 2003/0082120 A1 | 5/2003 | Milstein | |
| 2003/0130240 A1 | 7/2003 | Ashley | |
| 2003/0139380 A1 | 7/2003 | Ashley | |
| 2003/0199480 A1 | 10/2003 | Hayes et al. | |
| 2003/0229055 A1 | 12/2003 | Ashley | |
| 2004/0002481 A1 | 1/2004 | Ashley et al. | |
| 2004/0115261 A1 | 6/2004 | Ashley | |
| 2004/0127471 A1 | 7/2004 | Reisberg | |
| 2004/0228912 A1 | 11/2004 | Chang et al. | |
| 2005/0136107 A1 | 6/2005 | Patel et al. | |
| 2005/0148552 A1 | 7/2005 | Ryan et al. | |
| 2006/0293290 A1 | 12/2006 | Wortzman et al. | |

FOREIGN PATENT DOCUMENTS

| | | |
|---|---|---|
| CA | 2068366 | 11/1992 |
| CA | 2090561 | 2/1993 |
| EP | 0 184 389 | 6/1986 |
| EP | 0 418 565 | 3/1991 |
| EP | 0 558 913 | 9/1992 |
| GB | 2414668 | 12/2005 |
| WO | WO 93/18755 | 9/1993 |
| WO | WO 98/11879 | 3/1998 |
| WO | WO 98/55107 | 12/1998 |
| WO | WO 02/080932 | 10/2002 |
| WO | WO 03/088906 | 10/2003 |
| WO | WO 2004/012700 | 2/2004 |
| WO | WO 2004/078111 A2 | 9/2004 |

OTHER PUBLICATIONS

Gans et al. The Solubility and Complexing properties of Oxytetracycline and Tetracycline II, Journal of the American Pharmaceutical Association, Sci. Ed. 46, No. 10, Oct. 1957.

AAI International PROCORE® Technology, referencing patents issued prior to 2000.

AAI International PROSLO™ and PROSLO™ II Tablets Technology, referencing patents issued prior to 2000.

AAI International PROSORB® Technology, referencing patents issued prior to 2000.

Sheehan-Dare, et al., "A Double-blind Comparison of Topical Clindamycin and Oral Minocyclin in the Treatment of Acne Vulgaris", Acta Derm Venereol (Stockh), 70, pp. 534-537, 1990.

Solodyn (Minocycline HCl Extended Release Tablets) Labeling and package insert information, submitted with a New Drug Application approved May 8, 2006.

Gollnick, Harald, et al., "Management of Acne, A Report From a Global Alliance to Improve Outcomes in Acne", Supplement to Journal of The American Academy of Dermatology, Jul. 2003, vol. 49, No. 1, S1-37.

Leyden, James, J., "Absorption of minocycline hydrochloride and tetracycline hydrochloride", J. Am. Acad. Dermatol. 12:308-312, 1985.

Smith, Kelly, et al., "Safety of Doxycycline and Minocycline: A Systematic Review", Clinical Therapeutics, The International Peer-Reviewed Journal of Drug Therapy, vol. 27, No. 9, Sep. 2005, 1329-1342.

Leyden, James J., et al., "Comparison of Tazarotene and Minocycline Maintenance Therapies in Acne Vulgaris", Archives of Dermatology, May 2006, 605-612.

Leyden, James J, et al., "The antimicrobial effects in vivo of minocycline, doxycycline and tetracycline in humans", The Journal of Dermatological Treatment, Dec. 1996, vol. 7, No. 4, 223-225.

Leyden, James J., et al., "Tetracycline and Minocycline Treatment, Effects on Skin-Surface Lipid Levels and *Propionibacterium acnes*", Archives of Dermatology, 1982, vol. 118, 19-22.

Leyden, James J., et al., "*Pseudomonas aeruginosa* Gram-Negative Folliculitis", Archives of Dermatology, 1979, vol. 115, 1203-1204.

Leyden, James J., et al., "Clinical Considerations in the Treatment of Acne Vulgaris and Other Inflammatory Skin Disorders: Focus on Antibiotic Resistance", Cutis 2007 (suppl. 6), vol. 79, No. 65, 9-25.

Marks, Ronald, et al., (eds.) "Dermatologic Therapy in Current Practice", Chapter 3, 35-44 (2002).

International Search Report and Written Opinion mailed Dec. 5, 2007 pp. 1-18.

Office Communication dated Jun. 25, 2009 in U.S. Appl. No. 11/776,669.

Office Communication dated Jun. 10, 2009 in U.S. Appl. No. 11/776,676.

Office Communication dated May 29, 2009 in U.S. Appl. No. 11/776,711.

Office Communication dated May 29, 2009 in U.S. Appl. No. 11/944,186.

Office Communication dated Jun. 10, 2009 in U.S. Appl. No. 11/695,514.

Drugs.com, Drug information online, Minocin PAC product information, Aug. 2007.

Minocin Product Insert, Wyeth Pharmaceuticals Inc. Rev 10/05.

Prescribingreference.com, Prescribing Reference, Drug News—Minocin PAC for Acne (Oct. 11, 2006).

Physician's Desk Reference; MINOCIN®: Minocycline Hydrochloride for Oral Use; Physician's Desk Reference, 1989, pp. 1134-1136, 43rd Edition; Edward R. Barnhard, publisher, Medical Economics Co., Inc.; Oradell, NJ.

Office Communication dated Nov. 6, 2007 in U.S. Appl. No. 11/776,669.

Office Communication dated Jun. 17, 2008 in U.S. Appl. No. 11/776,669.

Office Communication dated Dec. 1, 2008 in U.S. Appl. No. 11/776,669.

Office Communication dated Nov. 6, 2007 in U.S. Appl. No. 11/776,676.

Office Communication dated Aug. 8, 2008 in U.S. Appl. No. 11/776,676.

Office Communication dated Nov. 6, 2007 in U.S. Appl. No. 11/776,711.

Office Communication dated Jun. 17, 2008 in U.S. Appl. No. 11/776,711.

Office Communication dated Nov. 17, 2008 in U.S. Appl. No. 11/944,186.

Office Communication dated Dec. 24, 2008 in U.S. Appl. No. 11/695,514.

Office Communication dated Jul. 22, 2008 in U.S. Appl. No. 11/695,528.

Office Communication dated Jul. 23, 2008 in U.S. Appl. No. 11/695,539.

Office Communication dated Dec. 23, 2008 in U.S. Appl. No. 11/695,539.

K. J. Gardner, et al., Comparison of serum antibiotic levels in acne patients receiving the standard or a modified release formulation of minocycline hydrochloride. Clinical and Experimental Dermatology, vol. 22, pp. 72-76, Jan. 1997.

Williams D. N., et al., Minocycline: Possible vestibular side-effects. Lancet. Sep. 28, 1974;2(7883):744-6.

U.S. Appl. No. 11/695,513, filed Apr. 2, 2007, Mitchell Wortzman.
U.S. Appl. No. 11/695,514, filed Apr. 2, 2007, Mitchell Wortzman.
U.S. Appl. No. 11/695,528, filed Apr. 2, 2007, Mitchell Wortzman.
U.S. Appl. No. 11/695,539, filed Apr. 2, 2007, Mitchell Wortzman.
U.S. Appl. No. 11/695,541, filed Apr. 2, 2007, Mitchell Wortzman.
U.S. Appl. No. 11/747,866, filed May 11, 2007, Mitchell Wortzman.

A Comparison of the Side Effects Produced by VECTRIN and DYNACIN After Normal Dosage. Clinical Acne Reviews, vol. 2 Oct. 1977.

Aditya K. Gupta et al., Solodyn (Minocycline HCl, USP) Extended-Release Tablets, LE JACQ, 291-292, Nov. Dec. 2006.

Allen N. Sapadin et al., Tetracyclines: Nonantibiotic properties and their clinical implications, American Academy of Dermatology, Inc., 258-265, Feb. 2006.

Bal L. Lokeshwar et al., Inhibition of Cell Proliferation, Invasion, Tumor Growth and Metastasis by an Oral Non-Antimicrobial Tetracycline Analog (COL-3) in a Metastatic Prostate Cancer Model, International Journal of Cancer: 98, 297-309 (2002).

Barbara Fingleton, CMT-3 CollaGenex, Current Opinion in Investigational Drugs, vol. 4, No. 12, 1460-1467, Dec. 2003.

Charles G. Hubbell et al. Efficacy of Minocycline Compared with Tetracycline in Treatment of Acne Vulgaris, Archives of Dermatology, vol. 118. 989-992, Dec. 1982.

Falk Ochsendorf, Systemic antibiotic therapy of acne vulgaris, Journal der Deutschen Dermatologischen Gesellschaft, 4:828-841, 2006.

Fleischer, A.B. et al. Safety and Efficacy of a New Extended-Release Formulation of Minocycline. Cutis 2006; 78 (suppl 4):21-31.

Gilbert Plott, Extended-Release Minocycline: Is Efficacy Dose-dependent in the Approved Dose Range?, Poster Presentation for the DUSA Pharmaceuticals, Inc. Medical Conferences and Trade Shows, Hawaii, Mar. 3-9, 2007.

Is minocycline overused in acne?, Drug and Therapeutics Bulletin. vol. 44 No. 8, 60-62, Aug. 2006.

James Q. Del Rosso, Clinical Significance of Brand Versus Generic Formulations: Focus on Oral Minocycline, Curtis, vol. 77, 153-156, Mar. 2006.

James Q. Del Rosso, et al. Weight-based Dosing of a Novel Antibiotic for Moderate-to-Severe Acne Vulgaris Offers Potential for Improved Safety and Tolerability, www.millennium.com/go/acne, Millennium CME Institute, Inc., 2006.

Jing Li et al, Evidence for Dissolution Rate-Limited Absorption of COL-3, a Matrix Metalloproteinase Inhibitor, Leading to the Irregular Absorption Profile in Rats after Oral Administration, Pharmaceutical Research, Vo. 19, No. 11, 1655-1662, Nov. 2002.

Muzharul M. Islam, A Nonantibiotic Chemically Modified Tetracycline (CMT-3) Inhibits intimal Thickening, American Journal of Pathology; vol. 163, No. 4, 1557-1566, Oct. 2003.

Plott, R. T. and Wortzman, M. Key Bioavailability Features of a New Extended-Release Formulation of Minocycline Hydrochloride Tablets. Cutis 2006; 78 (suppl 4):6-10.

Richard E. B. Seftor et al, Chemically modified tetracyclines inhibit human melanoma cell invasion and metastasis, Clinical & Experimental Metastasis, vol. 16, No. 3, 217-225 (1998).

Stewart, D.M. et al. Dose Ranging Efficacy of New Once-Daily Extended-Release Minocycline for Acne Vulgaris. Cutis 2006; 78 (suppl 4):11-20.

Ta et al., Effects of Minocycline on the Ocular Flora of Patients with Acne Rosacea or Seborrheic Blepharitis, Cornea vol. 22(6): 545-548,2003.

Adolfo C. Fernandez-Obregon, Azithromycin for the treatment of acne, International Journal of Dermatology 2000, 39, 45-50.

Arnold et al., Andrews' Diseases of the Skin: Clinical Dermatology, 8th Edition, p. 254, 1990.

Champion et al., "Disorders of the Sebaceous Glands," Textbook of Dermatology, 6th Edition, vol. 3, pp. 1958-1961, 1998.

Arndt et al., "What disorders present with inflamed skin?" Cutaneous Medicine and Surgery, An Intergrated Program in Dermatology, vol. 1, pp. 470-471, 1996.

Freedberg, et al., Fizpatrick's Dermatology in General Medicine, 5th Edition, vol. 1, pp. 77-778, 1999.

International Search Report/ Written Opinion dated Feb. 26, 2007, for PCT/US06/23761.

Pierard-Franchimont, et al. 2002. Lymecycline and Minocycline in Inflammatory Acne. Skin Pharmacol Appl Skin Physiol, 15:112-119.

Leyden, et al. 2006. New Extended-Release Minocycline. First Systemic Antibiotic Approved for the Treatment of Acne. A Supplement to Cutis, 78(4S):1-119.

Akamatsu, et al., "Effects of subminimal inhibitory concentrations of minocycline on neutrophil chemotactic factor production in comedonal bacteria, neutrophil phagocytosis and oxygen metabolism", Archives of Dermatological Research, vol. 283, 1991, pp. 524-528.

Bikowski, "Treatment of Rosacea With Doxycycline Monohydrate", vol. 66, Aug. 2000, pp. 149-152.

Brown, et al., "Diagnosis And Treatment Of Ocular Rosacea", Official Journal of American Academy of Ophthalmology, vol. 85, Aug. 1978, pp. 779-786.

Fingleton, "CMT-3 CollaGenex", Current Opinion in Investigational Drugs, vol. 4, No. 12, Dec. 2003, pp. 1460-1467.

Golub, et al., "Tetracyclines Inhibit Connective Tissue Breakdown: New Therapeutic Implications for an Old Family of Drugs", Critical Reviews in Oral Biology and Medicine, vol. 2, No. 2, 1991, pp. 297-322.

Illig, "Positive Side Effects of Antibiotic and Antimicrobial Substances in Therapy", Infection, vol. 7, Suppl. 6, 1979, pp. S 584-588. (with English-language translation).

Millar, MB, ChB., et al., "A general practice study investigating the effect of minocycline (Minocin) 50 mg bd for 12 weeks in the treatment of acne vulgaris", British Journal of Clinical Practice, vol. 41, No. 8, Aug. 1987, pp. 882-886.

Webster, "Inflammation in acne vulgaris", Journal of the American Academy of Dermatology, vol. 33, No. 2, part 1, Aug. 1995, pp. 247-253.

Webster, et al., "Suppression of Polymorphonuclear Leukocyte Chemotactic Factor Production in *Propionibacterium acnes* by Subminimal Inhibitory Concentrations of Tetracycline, Ampicillin, Minocycline, and Erythromycin", Antimicrobial Agents and Chemotherapy, vol. 21, No. 5, May 1982, pp. 770-772.

Akamatsu, et al., "Effect of Doxycycline on the Generation of Reactive Oxygen Species: *A Possible Mechanism of Action of Acne Therapy with Doxycycline*"; Acta Derm Venereol (Stockh), 1992; 72: 178-179.

Japanese Publication No. JP4020064374A; "Compounds Having Retinoid Like Activity and Pharmaceutical Composition Containing the Same", Jan. 10, 1990.

Darrah, et al., "An open multicentre study to compare fusidic acid lotion and oral minocycline in the treatment of mild-to-moderate acne vulgaris of the face", European Journal of Clinical Research, 1996, vol. 8, pp. 97-107.

Hersle, et al., "Minocycline in Acne Vulgaris: a Double-Blind Study", Current Therapeutic Research, Mar. 1976, vol. 19, No. 3, pp. 339-342.

Millar, et al., "A general practice study investigating the effect of minocycline (Minocin) 50 mg bd for 12 weeks in the treatment of acne vulgaris", The British Journal of Clinical Practice, Aug. 1987, vol. 41, No. 8, pp. 882-886.

Dreno, et al., "Multicenter Randomized Comparative Double-Blind Controlled Clinical Trial of the Safety and Efficacy of Zinc Gluconate versus Minocyclin Hydrochloride in the Treatment of Inflammatory Acne vulgaris", Dermatology, 2001, vol. 203, pp. 135-140.

Sheehan-Dare, et al., "A Double-blind Comparison of Topical Clindamycin and Oral Minocyclin in the Treatment of Acne Vulgaris", Acta Derm Venereol (Stockh), 70, pp. 534-537, Jan. 1, 1990.

Hubbell, et al., "Efficacy of Minocycline Compared With Tetracycline in Treatment of Acne Vulgaris", Aren Dermatol, vol. 118, Dec. 1982, pp. 989-992.

Harrison, "A comparison of doxycycline and minocycline in the treatment of acne vulgaris", Clinical and Experimental Dermatology, 1998, vol. 13, pp. 242-244.

Smit, "Minocycline versus Doxycycline in the Treatment of Acne vulgaris", Dermatologica, vol. 157, 1978, pp. 186-190.

Garner SE, et al., "Minocycline for acne vulgaris: efficacy and safety", (Cochrane Review), The Cochrane Library, issue 1, 2004, Chichester, UK: John Wiley & Sons, Ltd.

Jonas, et al., "Minocycline", Therapeutic Drug Monitoring, vol. 4, 1982, pp. 137-145.

Freeman, et al., "Therapeutic Focus Minocycline in the treatment of acne", BJCP, Mar. 1989, vol. 43, pp. 112-114.

Kelly, et al., "Metabolism and Tissue Distribution of Radiosotopically Labeled Minocyclin", Toxicology and Applied Pharmacology, 1967, vol. 11, pp. 171-183.

Schach Von Wittenau, et al "The Distribution of Tetracyclines in Tissues of Dogs After Repeated Oral Administration", The Journal of Pharmacology and Experimental Therapeutics, 1965, vol. 152, No. 1, pp. 164-169.

Agwuh, K.N., et al., "Pharmacokinetics of the tetracyclines including glycylcyclines," J. Antimicrobial Chemotherapy vol. 58, 256-265 (Jul. 1, 2006).

American Hospital Formulary Service, AHFS Drug Information 446-448 (2003).

Cartwright, A.C., et al., "A comparison of the bioavailability of minocycline capsules and film-coated tablets," J. Antimicrobial Chemotherapy vol. 1, 317:322 (1975).

Cullen, S.I., et al., "Minocycline therapy in acne vulgaris", Cutis vol. 17, No. 6, 1208-1214 (1976).

Del Rosso, J.Q., "A status report on the use of subantimicrobial-dose doxycycline: a review of the biologic and antimicrobial effects of the tetracyclines," Cutis 118-122 (Jun. 1, 2004).

Del Rosso, J.Q., "What's new in the Medicine Cabinet?", Supplement to the Feb. 2005 Skin and Aging Conference, pp. 3-6.

dePaz, S., et al., "Severe hypersensitivity reaction to minocycline", Invest. Allergol. Clin. Immunol., vol. 9, No. 6, 403-404 (1999).

Eady, A.E., et al., "Is antibiotic resistance in cutaneous propionibacteria clinically relevant?", Amer. J. Clin. Dermatol., vol. 4, No. 12, 813-831 (2003).

Goldstein, N.S., et al., "Minocycline as a cause of drug-induced autoimmune hepatitis", Amer. J. Clin. Pathol., vol. 114, 591-598 (2000).

Gump, D.W., et al., "Side effects of minocycline: different dosage regimens," Antimicrobial Agents and Chemotherapy, vol. 12, No. 5, 642-646 (Nov. 1977).

Healy, N., et al., "Fortnightly review, acne," BMJ vol. 308, 831-833 (1994).

Johnson, B.A., et al., "Use of systemic agents in the treatment of acne vulgaris," Am. Fam Physician vol. 62,1823-1830, 1835-1836 (Oct. 15, 2000).

Lawrenson, R.A., et al., "Liver damage associated with minocycline use in acne", Drug Safety, vol. 23, No. 4, 333-349 (2000).

MacDonald, H., et al., "Pharmacokinetic studies on minocycline in man," American Cyanamid (Lederle Laboratories division) 852-861 (1973).

Shalita, A., "The integral role of topical and oral retinoids in the early treatment of acne," J. European Acad. Derm. Venereol. vol. 15, Suppl. 3, 43-49 (2001).

Minocycline Hydrochloride Capsules, USP Bioequivalence Study (Admitted Prior Art).

Office Communication dated Nov. 6, 2009 in Chinese Pat. Appl. Ser. No. 2006800224203 (with English translation).

Yang, Jian, et al., LingNan Skin Disease Magazine, No. 1, p. 38 (1994) (with English translation).

Extended European Search Report in European Application No. 06773507.6, dated Jul. 1, 2009.

Examination Report in NZ Application No. 564093, dated Oct. 29, 2009.

* cited by examiner

METHOD FOR THE TREATMENT OF ACNE

FIELD OF THE INVENTION

This invention relates to the treatment of acne vulgaris, commonly known simply as "acne." Acne is a disease of the skin in which the pilosebaceous structures of the skin become inflamed, leading to the formation of comedones, pustules and nodules. Acne can lead to permanent scarring in severe cases.

It is generally believed that acne arises when hyperkeratosis of the pilosebaceous structure wholly or partially blocks the opening of the structure, resulting in comedones filled with sebum, keratin, and *Propionibacterium acnes*. These lesions are commonly identified as acne. *P. acnes* naturally occurs in normal skin, but is especially and characteristically present in acne lesions. It is believed that metabolic byproducts and waste from *P. acnes* within the pilosebaceous structures cause or contribute to the inflammation of acne lesions.

Conventional acne treatments have taken many forms. Topical keratolytic agents, such as salicylic acid are sometimes used. Keratolytic agents are thought to encourage the opening up of blocked pilosebaceous structures, thereby reducing conditions that are favorable to inflammation. Benzoyl peroxide, an anti-microbial, remains a popular and effective treatment. Topical antibiotics, such as clindamycin, which are effective against *P. acnes*, have also been used with a view towards preventing the formation of metabolic byproducts from this organism. Topical retinoids such as tretinoin have also been used in the treatment of acne.

Systemic (i.e. non-topical) treatments for acne include the use of oral antibiotics in more serious cases. These treatments are directed towards the reduction in the amount *P. acnes* in the skin, especially the pilosebaceous structures, and seek to reduce the inflammation caused by waste materials and metabolic byproducts from these organisms. Tetracycline antibiotics are most commonly used for this purpose. These include tetracycline, minocycline and doxycycline. Erythromycin is also sometimes used.

Standard oral minocycline therapy for acne in pediatric patients calls for the administration of a 4 mg/kg initial loading dose, and a 2 mg/kg dose every 12 hours thereafter. This results in a dose of 6 mg/kg on the first day of treatment and a 4 mg/kg dose each day thereafter. In adults, a 200 mg initial dose is followed by a 100 mg dose every 12 hours thereafter. In a typical patient, this results in about a 4.5 mg/kg dose on the first day of treatment, and 3.0 mg/kg dose each day thereafter.

In cases where acne does not respond to oral antibiotic treatment, oral isotretinoin is sometimes used. While effective, isotretinoin is also powerfully teratogenic, and women of childbearing age are required to use multiple methods of contraception while taking the drug.

While oral tetracycline antibiotics remain a highly favored and widely used treatment for more serious cases of acne, it is not without side effects. Vestibular side effects, including extreme dizziness and concomitant nausea, can be so severe as to result in discontinuance of tetracycline therapy. Long term use can sometimes result in vaginal candidisis, esophageal erosions and in antibiotic resistant infections.

Some recent research has indicated that very low doses of oral tetracycline can result in some improvement of acne even though the dose of tetracycline is too low to have an antibiotic effect. This observation has been attributed to an anti-inflammatory effect of tetracycline compounds. This effect has been reported to have been observed even where a chemically modified tetracycline that have no antibiotic properties are used. The use of tetracycline antibiotics at a dose too low to have an antibiotic effect or the use of modified tetracycline having no antibiotic properties as treatments for acne has never been approved by any drug regulatory agency.

SUMMARY OF THE INVENTION

According to the present invention, a method is provided for the treatment of acne in which an antibiotically effective dose of an oral tetracycline, such as minocycline, is provided. This dose is approximately 1 milligram per kilogram of body weight (1 mg/kg), without an initial loading dose of antibiotic. This antibiotic dosing regimen has been found to be as effective as a conventional dosing regimen incorporating a significant initial loading dose and higher subsequent doses. However, the dosing method of the current invention produces far fewer side effects.

In another aspect of this invention, the oral tetracycline is provided in a dosage form that provides for the continued release of the antibiotic between doses, as opposed to an immediate or nearly immediate release of the drag.

DETAILED DESCRIPTION OF THE INVENTION

According to the present invention, acne vulgaris is treated by the use of an oral tetracycline antibiotic, preferably minocycline. This antibiotic is administered in an antibiotically effective amount of approximately 1.0 milligram per kilogram of body weight per day (1.0 mg/kg/day). While this may be accomplished by the use of divided doses, it is preferred that the tetracycline antibiotic be delivered in a single daily dose. This treatment regime is initiated without a loading dose, and is continued until resolution or substantial resolution of the patient's acne. The course of treatment typically lasts 12 to up to 60 weeks, but will be adjusted according to the disease status and other medical conditions of each patient in the exercise of ordinary good clinical judgment by the patient's health care provider.

Controlled, double-blinded studies were undertaken to determine the effectiveness of this invention. Treatment of 473 patients with acne was undertaken according to the present invention. Placebos were provided to 239 patients. The effectiveness of the invention in treating acne vulgaris is shown in Table 1.

TABLE 1

Total Lesion Counts

|  | Total Lesions | Total Lesions (as Percent of Baseline) |
| --- | --- | --- |
| Baseline (mean) | 169.3 | 100 |
| Day 28 (mean) | 134.0 | 78 |
| Day 56 (mean) | 119.3 | 69 |
| Day 84 (mean) | 112.3 | 66 |

Inflammatory Lesion Counts

|  | Inflammatory Lesions | Inflammatory Lesions (as Percent of Baseline) |
| --- | --- | --- |
| Baseline (mean) | 77.4 | 100 |
| Day 28 (mean) | 52.1 | 66 |
| Day 56 (mean) | 44.3 | 56 |
| Day 84 (mean) | 41.9 | 53 |

While effective as a treatment for acne, this resulted in almost no side effects above those observed with a placebo, as shown in Table 2.

TABLE 2

% Subjects with Adverse Events

| | Minocycline | Placebo |
|---|---|---|
| At least One Adverse Event | 56.2 | 54.1 |
| At Least One Serious Adverse Event | 0.4 | 0 |
| Blood/Lymphatic System Disorders | 0.3 | 0.3 |
| Cardiac Disorders | 0.3 | 0 |
| Ear and Labyrinth Disorders | 3.6 | 3.3 |
| Endocrine Disorders | 0.3 | 0 |
| Eye Disorders | 2.2 | 2.7 |
| Gastrointestinal Disorders | 21.2 | 26.1 |
| General Disorders and Administrative Site Conditions | 13.8 | 10.4 |
| Immune System Disorders | 0.7 | 2.5 |
| Infections and Infestations | 9.3 | 11.0 |
| Laboratory Blood Abnormalities | 0.7 | 1.1 |
| Metabolism and Nutrition Disorders | 0.6 | 0.3 |
| Musculoskeletal and Connective Disorders | 4.6 | 3.6 |
| Neoplasms Benign, Malignant and Unspecified | 0.1 | 0 |
| Nervous System Disorders | 29.2 | 25.8 |
| Psychiatric Disorders | 6.4 | 7.1 |
| Renal and Urinary Disorders | 0.3 | 0.5 |
| Reproductive System and Breast Disorders | 0.7 | 0.3 |
| Respiratory, Thoracic and Mediastinal Disorders | 5.3 | 6.9 |
| Skin and Subcutaneous Tissue Disorders | 8.6 | 7.1 |
| Vascular Disorders | 1.0 | 0.3 |

The effectiveness of this invention can be seen by comparing the above efficacy data with published data on the effectiveness of conventional tetracycline treatments for acne in the reduction of total acne lesions and in the reduction of inflammatory lesions. See, e.g. Hersel & Gisslen, "Minocycline in Acne Vulgaris: A Double Blind Study," Current Therapeutic Research, 1976.

Because of the variations in body weight encountered in clinical practice, in the actual practice of this invention it is not practical to provide every patient with exactly 1 mg/kg/day of oral tetracycline antibiotic. However, it is acceptable to approximate this dose by providing the patient with from 0.5 to 1.5 mg/kg/day although from 0.7 to 1.3 mg/kg/day is preferred, and 1.0 mg/kg/day is ideal.

While it can be effective to provide the oral tetracycline antibiotic in divided doses taken over the course of a day (e.g. twice or three times a day), it is preferable to provide the oral tetracycline antibiotic in a dosage form that releases the antibiotic slowly during the course of a day so that once-a-day dosing is possible. While delayed release dosage forms are known in the art, the formulation of them is far from predictable and the selection of a specific delayed release formulation is accomplished more by trial and error than by mathematical prediction based on known properties of delay release agents. No delayed release product useful in the present invention has been known heretofore.

It has been discovered that the ratio of fast dissolving carriers to slow dissolving carriers in the core caplet is important in obtaining a dissolution profile that enables once-a-day dosing in accordance with the present invention. By keeping the ratio of these components within a certain range, one may obtain this result.

The fast dissolving carrier is any binder, vehicle, or excipient that quickly dissolves in an aqueous physiological medium, such as gastric fluid, thereby tending to quickly release the active ingredient. Lactose, its salts and hydrates are good examples of such components. It has been observed that sometimes a portion of the fast dissolving components are formulated in a manner that results in the complete or partial encapsulation or inclusion or coating of these fast-dissolving materials in granules of slow-dissolving materials. These encapsulated materials are excluded from the calculation of the above mentioned ratio of fast-dissolving to slow dissolving components.

A slow dissolving carrier is any binder, vehicle, or excipient that dissolves slowly over the course of hours and perhaps a day, thereby slowing the release of the active ingredient. Examples of such components are polyvinyl pyrrolidone, polyvinyl acetate, microcrystalline cellulose, methyl cellulose, ethyl cellulose, hydroxypropyl cellulose, hydroxypropylmethyl cellulose, or waxy or lipid-based tableting agents such as magnesium stearate or calcium stearate. Outer "enteric" coatings are excluded from this amount when calculating the above-mentioned ratio.

Insoluble carriers are binders, vehicles, or excipients that are practically insoluble in physiological fluids, such as gastric fluid, and includes compounds, such as silicon dioxide and talc.

While the exact formulation of these dosage forms can vary, it has been observed that it is advantageous to formulate them so that the ratio of fast dissolving carriers to slow dissolving carriers is from 0.30 to 0.50, and preferably from 0.35 to 0.45. A ratio of about 0.36 to 0.40 is particularly preferable.

Dosage forms, such as capsules, tablets, and caplets that release 25 to 52% of the antibiotics within 1 hour, 53 to 89% in 2 hours, and at least 90% within 4 hours are suited to the once-a-day dosage regimen contemplated by the current inventories. More preferably, 30 to 52% of the antibiotic is released within 1 hour, 53 to 84% within 2 hours, and at least 85% within 4 hours.

Alternatively, the oral tetracycline antibiotic may be delivered in a dosage form that releases the antibiotic in such a way that the maximum blood concentration of the antibiotic ($C_{max}$) is reached at about 3.5 hours after administration ($T_{max}$). In actual practice of the invention, the $C_{max}$ should be reached between 2.75 and 4.0 after administration, more preferably between 3.0 and 3.75 after administration.

As examples of such a once-a-day formulation, one may use the following:

| Component | Quantity (mg) |
|---|---|
| 135 mg Caplet | |
| Minocycline (as hydrochloride) (dry weight) | 145.8 |
| Lactose Monohydrate (intragranular) | 107.4 |
| Lactose Monohydrate (extragranular) | 43.8 |
| Total Lactose Monohydrate | 151.2 |
| HPMC | 94 |
| Silicon Dioxide | 3 |
| Mg. Stearate | 6 |
| 45 mg Caplet | |

-continued

| Component | Quantity (mg) |
|---|---|
| Minocycline (as hydrochloride) (dry weight) | 48.6 |
| Lactose Monohydrate (intragranular) | 192.2 |
| Lactose Monohydrate (extragranular) | 42.2 |
| Total Lactose Monohydrate | 234.40 |
| HPMC | 108 |
| Silicon Dioxide | 3 |
| Mg. Stearate | 6 |

Each of these components is combined in a conventional fashion, compressed in a tabletting apparatus, and then provided in a conventional manner with a suitable coating, such as, without limitation Opadry II and optional coloring.

What is claimed is:

1. A method of treating acne vulgaris, comprising administering to a patient suffering from acne vulgaris an amount of a continuous slow release oral dosage form based on body weight of the patient, said continuous slow release oral dosage form comprising:
   an amount of an oral minocycline antibiotic that provides the patient, upon administration once daily without a loading dose, with 0.7 mg/kg/day to 1.3 mg/kg/day of said oral minocycline antibiotic; and
   a delivery vehicle having a first lactose monohydrate, a second lactose monohydrate, and a slow dissolving carrier, wherein said first lactose monohydrate is encapsulated by said slow dissolving carrier, wherein said second lactose monohydrate and said slow dissolving carrier are present at a weight ratio of about 0.3 to about 0.5,
   wherein said delivery vehicle releases said oral minocycline antibiotic at a release rate of:
   A) about 25 to about 52% within about 1 hour about 53 to about 89% within about 2 hours, and at least about 90% within about 4 hours; or
   B) about 30 to about 52% within about 1 hour about 53 to about 84% within about 2 hours, and at least about 85% within about 4 hours,
   wherein said release rate is measured in an aqueous physiological medium.

2. The method of claim 1, wherein said amount of 0.7 mg/kg/day to 1.3 mg/kg/day of said oral minocycline antibiotic is about 1 mg/kg/day.

3. The method of claim 1, wherein said delivery vehicle releases said oral minocycline antibiotic in such a manner that said oral minocycline antibiotic reaches the $C_{max}$ in the person's blood from about 3.5 hours after administration.

4. The method of claim 1, wherein said second lactose monohydrate and said slow dissolving carrier are present at a weight ratio of about 0.36 to about 0.40.

5. A method of treating acne vulgaris, comprising
   administering to a patient suffering from acne vulgaris an amount of a continuous slow release oral dosage form based on body weight of the patient, the continuous slow release dosage form comprising:
   an amount of an oral minocycline antibiotic that provides the patient, upon administration once daily without a loading dose, with 0.7 mg/kg/day to 1.3 mg/kg/day of said oral minocycline antibiotic; and
   a delivery vehicle having a fast dissolving carrier and a slow dissolving carrier, wherein the fast dissolving carrier has a first portion thereof that is encapsulated by the slow dissolving carrier and a second portion thereof that is not encapsulated by the slow dissolving carrier, and wherein the second portion of the fast dissolving carrier and the slow dissolving carrier are present at a weight ratio of 0.3 to 0.5, wherein the delivery vehicle releases said oral minocycline antibiotic at a release rate of:
   A) about 25 to about 52% within about 1 hour about 53to about 89% within about 2 hours, and at leastabout 90% within about 4 hours; or
   B) about 30 to about 52% within about 1 hour about 53 to about 84% within about 2 hours, and at leastabout 85% within about 4 hours,
   wherein the release rate is measured in an aqueous physiological medium.

6. The method of claim 1, wherein said slow dissolving carrier is hydroxypropyl methylcellulose.

* * * * *